United States Patent
Muskett

(10) Patent No.: US 6,255,527 B1
(45) Date of Patent: Jul. 3, 2001

(54) CARBONYLATION OF METHANOL TO ACETIC ACID WITH CARBON MONOXIDE FLOW CONTROLS

(75) Inventor: Michael James Muskett, East Yorkshire (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/389,488

(22) Filed: Sep. 3, 1999

(30) Foreign Application Priority Data

Sep. 3, 1998 (GB) .................................................. 9819079

(51) Int. Cl.⁷ .................................................. C07C 51/12
(52) U.S. Cl. ............................................. 562/519; 562/607
(58) Field of Search .................................. 562/519, 607; 422/105

(56) References Cited

U.S. PATENT DOCUMENTS

| | | |
|---|---|---|
| 3,772,380 | 11/1973 | Paulik et al. . |
| 4,255,591 | * 3/1981 | Makin et al. . |
| 5,210,322 | * 5/1993 | King et al. . |
| 5,352,415 | 10/1994 | Ochiai . |
| 5,510,524 | * 4/1996 | Garland et al. . |
| 5,917,089 | * 6/1999 | Howard . |

FOREIGN PATENT DOCUMENTS

| | | |
|---|---|---|
| 17 67 150 | 5/1972 | (DE) . |
| 0 384 652 | 8/1990 | (EP) . |
| 0 391 680 | 10/1990 | (EP) . |
| 0 616 997 | 9/1994 | (EP) . |
| 0 618 183 | 10/1994 | (EP) . |
| 0 618 184 | 10/1994 | (EP) . |
| 0 618 184 A1 | 10/1994 | (EP) . |
| 0 657 386 | 6/1995 | (EP) . |
| 0 657 386 A1 | 6/1995 | (EP) . |
| 95/31426 | 11/1995 | (EP) . |
| 0 687 662 A2 | 12/1995 | (EP) . |
| 1 233 121 | 5/1971 | (GB) . |
| 1 234 641 | 6/1971 | (GB) . |
| 95/1426 | 11/1995 | (WO) . |

OTHER PUBLICATIONS

Howard et al, "$C_1$ to acetyls: catalysis and process", Catalysis Today, vol. 18, pp. 325–354 (1993).

* cited by examiner

Primary Examiner—Paul J. Killos
Assistant Examiner—Robert W. Deemie
(74) Attorney, Agent, or Firm—Nixon & Vanderhye

(57) ABSTRACT

A method of controlling the carbon monoxide flow to a reactor wherein acetic acid is produced continuously by feeding carbon monoxide through a control valve and methanol and/or a reactive derivative thereof, there being maintained in the reactor a liquid reaction composition comprising at least 5% w/w methyl acetate, a finite concentration of water, from 1 to 30% w/w methyl iodide, a Group VIII noble metal catalyst, optionally at least one promoter and acetic acid comprising the remainder of the composition which method comprises the steps of:

Figure 1:
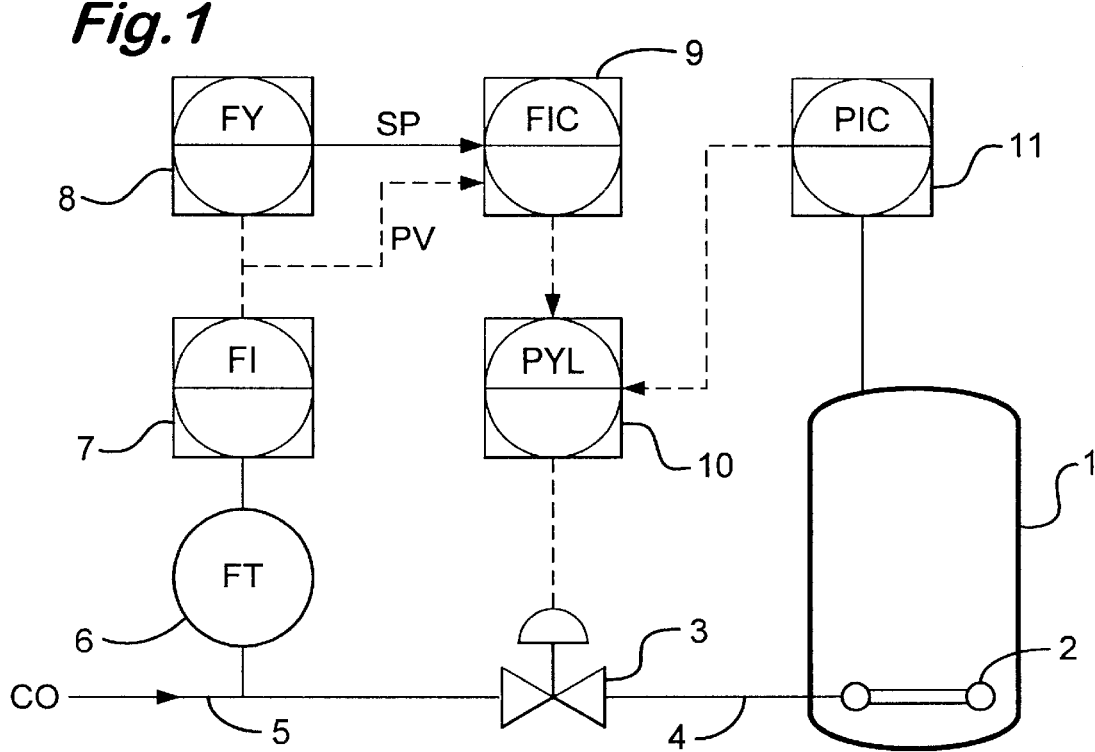

(i) measuring the carbon monoxide flow through the control valve;
(ii) performing a background calculation to arrive at a time-averaged carbon monoxide flow rate;
(iii) adding a constant value to the time-averaged carbon monoxide flow to arrive at a maximum allowable carbon monoxide flow rate; and
(iv) feeding information comprising the calculated maximum allowable carbon monoxide flow rate to a control system which operates in a manner such that the carbon monoxide flow rate to the reactor can not exceed the calculated maximum flow rate at any time.

12 Claims, 2 Drawing Sheets

CARBONYLATION OF METHANOL TO ACETIC ACID WITH CARBON MONOXIDE FLOW CONTROLS

The present invention relates in general to a carbonylation process for the production of acetic acid and in particular to a process for the production of acetic acid by the carbonylation of methanol and/or a reactive derivative thereof in the presence of a Group VIII noble metal as catalyst, a hydrocarbyl halide as co-catalyst and optionally a promoter.

Homogeneous liquid phase processes for the production of acetic acid by the Group VIII noble metal catalysed, hydrocarbyl halide co-catalysed reaction of carbon monoxide are well-known. The process using rhodium as the noble metal catalyst is described in, for example GB-A-1,233,121; EP-A-0384652; and EP-A-0391680. The process using iridium as the noble metal catalyst is described in, for example, GB-A-1234121, U.S. Pat. No. 3,772,380, DE-A-1767150, EP-A-061997, EP-A-0618184, EP-A-0618183, EP-A-0657386 and WO-A-95/31426. Carbonylation processes for the production of acetic acid in the presence of either a rhodium or an iridium carbonylation catalyst are operated on a commercial scale at several locations worldwide.

Howard et al in Catalysis Today, 18 (1993) 325–354 describe rhodium and iridium-catalysed carbonylation of methanol to acetic acid. The continuous rhodium-catalysed, homogeneous methanol carbonylation process is said to consist of three basic sections; reaction, purification and off-gas treatment. The reaction section comprises a stirred tank reactor, operated at elevated temperature and pressure, and a flash vessel. Liquid reaction composition is withdrawn from the reactor and is passed through a flashing valve to a flash tank where the majority of the lighter components of the liquid reaction composition (methyl iodide, methyl acetate and water) together with product acetic acid are vaporised. The vapour fraction is then passed to the purification section whilst the liquid fraction (comprising the rhodium catalyst in acetic acid) is recycled to the reactor (cf FIG. 2 of Howard et al). The purification section is said to comprise a first distillation column (the light ends column), a second distillation column (the drying column) and a third distillation column (the heavy ends column) (cf FIG. 3 of Howard et al). In the light ends column methyl iodide and methyl acetate are removed overhead along with some water and acetic acid. The vapour is condensed and allowed to separate into two phases in a decanter, both phases being returned to the reactor. Wet acetic acid is removed from the light ends column as a sidedraw and is fed to the drying column where water is removed overhead and an essentially dry acetic acid stream is removed from the base of the distillation zone. From FIG. 3 of Howard et al it can be seen that the overhead water stream from the drying column is recycled to the reaction section. Heavy liquid by-products are removed from the base of the heavy ends column with product acetic acid being taken as a sidestream.

It is with the reaction section and the operation thereof that the present invention is concerned. In terms of the process outlined above it is specifically with the reactor and its operation that the invention is primarily concerned. During continuous operation it has been customary to feed carbon monoxide on demand under pressure control, and methanol to a reactor containing a liquid composition comprising specific standing concentration of methyl acetate, water, methyl iodide co-catalyst, Group VIII noble metal catalyst, optionally one or more promoters, and comprising the remainder of the composition acetic acid. In the reactor carbonylation occurs to produce acetic acid which is removed in the liquid reaction composition, and thereafter acetic acid is recovered as hereinbefore described. Unconverted carbon monoxide is vented from the reactor and after recovery of volatile components therefrom is generally discarded. At methyl acetate concentrations in the liquid reaction composition of less than about 6% w/w, which levels are generally associated with the use of rhodium catalysts, practically all the methyl acetate is converted by carbonylation to acetic acid. Under such circumstances little, if any, difficulty is experienced in controlling the reactor temperature. However, at methyl acetate concentrations of at least 5% w/w, typically 8% w/w or greater, which levels are generally associated with the use of iridium catalysts, not all the methyl acetate in the liquid reaction composition is converted and the potential therefore exists for uncontrollable exotherms arising from an ever increasing demand for carbon monoxide and the presence of unconverted methyl acetate reactant. Under such circumstances the plant may trip, which is undesirable because it interrupts production. Unsteady reactor temperature also leads to instability in reactor carbon monoxide uptake. This leads to the requirement to vent carbon monoxide to flare for control purposes, resulting in loss of carbon monoxide conversion efficiency. Reaction temperature control at high methyl acetate concentrations is therefore a significant problem. A solution to the problem is the provision of a mechanism to limit the amount of carbon monoxide available to the reactor to avoid uncontrollable exotherms.

Accordingly the present invention provides a method of controlling the carbon monoxide flow to a reactor wherein acetic acid is produced continuously by feeding carbon monoxide through a control valve and methanol and/or a reactive derivative thereof, there being maintained in the reactor a liquid reaction composition comprising at least 5% w/w methyl acetate, a finite concentration of water, from 1 to 30% w/w methyl iodide, a Group VIII noble metal catalyst, optionally at least one promoter and acetic acid comprising the remainder of the composition which method comprises the steps of:

(i) measuring the carbon monoxide flow through the control valve;

(ii) performing a background calculation to arrive at a time-averaged carbon monoxide flow rate;

(iii) adding a constant value to the time-averaged carbon monoxide flow to arrive at a maximum allowable carbon monoxide flow rate; and (iv) feeding information comprising the calculated maximum allowable carbon monoxide flow rate to a control system which operates in a manner such that the carbon monoxide flow rate to the reactor can not exceed the calculated maximum flow rate at any time.

In one embodiment the method comprises activating the control valve through a low signal selector responsive to inputs from either a reactor pressure controller or a carbon monoxide feed flow controller, the flow-controller being governed by the maximum allowable carbon monoxide flow rate, as calculated by a calculation block functioning to determine a time-averaged carbon monoxide flow rate and add a constant value thereto, the input to the signal selector and hence operation of the control valve being through the flow controller when the carbon monoxide feed rate to the reactor is higher than the maximum allowable carbon monoxide flow rate and through the pressure controller when the carbon monoxide feed rate to the reactor is lower than the maximum allowable carbon monoxide flow rate. In this embodiment the flow-controller is not normally in control of the flow valve operation because the flow rate is normally below the maximum allowable carbon monoxide flow rate as determined by the calculation block and the pressure controller is operative through the selector. In the event of a reactor disturbance involving greater carbon monoxide uptake the carbon monoxide flow output becomes lower than the pressure controller output and the flow controller takes control through the selector.

There are other ways in which the method of the present invention may be applied. Thus, for example, the flow controller may be in permanent charge of operation of the control valve in which case the calculation block sets a value for the maximum allowable carbon monoxide flow such that the flow through the control valve does not exceed this value.

An advantage of the process according to the present invention is that satisfactory control of the process can be achieved at high methyl acetate conversions, thereby improving plant stability and, in consequence, reliability.

The maximum allowable carbon monoxide flow rate suitably conforms to the following formula:

$$FC_{sp} = F_{av} + X \qquad (I)$$

wherein $FC_{sp}$=maximum allowable carbon monoxide flow rate i.e. the flow controller set-point, $F_{av}$=the carbon monoxide flow (in tons/hour) over a specified immediately preceding time period X=a pre-determined amount in the range from 0.1 to to 1.0 tons/hour.

The specified immediately preceding time period may be any desired time. Ten minutes is a suitable time. A suitable value for X is for example 2.5% $F_{av}$. Thus, for example, if $F_{av}$ is 20 tons/hour, X is suitably 0.5 tons/hour and $FC_{sp}$ is 20.5 tons/hour.

In a preferred embodiment of the present invention in addition to controlling the carbon monoxide flow into the reactor, the flow of high pressure vent gas is used to control the reactor pressure. Suitably, a method for achieving this comprises activating the high pressure vent gas control valve through a signal selector responsive to inputs from either a flow controller or a second pressure controller, the second pressure controller being governed by a set-point which is below the pressure of the first pressure controller, referred to hereinbefore, the input to the signal selector and hence operation of the control valve being through the second pressure controller when the reactor pressure falls below the set-point and through the flow controller when the reactor pressure is equal to or above the set-point. Optionally, this may also be achieved by means of a set point high limit to the high pressure ventgas controller, or by other process control techniques.

The set-point of the second pressure controller is suitably set from 1.0 to 5.0%, for example about 2%, lower than that of the first pressure controller. Thus for example, if the set-point of the first pressure controller is set at 27.6 bar, the set-point of the second pressure controller may suitably be set at 27.1 bar. Normally, the flow controller is in charge of the high pressure vent gas control valve.

There is fed to the reactor methanol and/or a reactive derivative thereof Reactive derivatives of methanol include methyl acetate, dimethyl ether and methyl iodide.

There is maintained in the reactor a liquid reaction composition comprising at least 5% w/w, typically at least 8% w/w, methyl acetate, a finite concentration of water, from 1 to 30% w/w methyl iodide, a Group VIII noble metal catalyst, optionally at least one promoter and acetic acid comprising the remainder of the composition.

Although, for example, rhodium may be used as the Group VIII noble metal catalyst at high methyl acetate concentrations in the liquid reaction composition of at least 5%, typically at least 8% w/w, such high concentrations are much more characteristic of the use of iridium catalysts. The method of controlling the carbon monoxide flow to the reactor is therefore preferably used in combination with an iridium catalyst. The concentration of methyl acetate may suitably be up to 30% w/w, preferably up to 25% w/w. Typically the concentration of methyl acetate may be in the range from to 20% w/w.

Water is present in the liquid reaction composition in a finite concentration, that is at least 0.1% w/w. Suitably water may be present in an amount from 0.1 to 30% w/w, typically from 0.1 to 20% w/w, for example from 0.1 to 10% w/w. Preferably water is present in an amount from 1 to 6% w/w. Water may be formed in situ in the carbonylation reaction, for example by the esterification reaction between methanol and/or reactive derivative thereof reactant and carboxylic acid product. Water may be introduced to the carbonylation reactor together with or separately from the other liquid reactants. Water may be separated from the liquid reaction composition withdrawn from the reactor and recycled in controlled amounts to maintain the required concentration in the carbonylation reaction composition.

Methyl iodide co-catalyst may suitably be present in the liquid reaction composition in an amount in the range from 1 to 30% w/w, more preferably from 1 to 20% w/w, for example from 1 to 10% w/w.

The Group VIII noble metal may be present in the liquid reaction composition in any form which is soluble in the composition. It may be added to the liquid reaction composition in any form which is soluble in the composition or is convertible to soluble form. Iridium, for example, is preferably used as a chloride-free compound such as a carboxylate salt, e.g. the acetate, which is soluble in one or more of the liquid reaction components, e.g. water and/or acetic acid, and so may be added as a solution therein. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2I_2Br_2]^-H^+$, $[Ir(CO)_2I_2]^-H^+$, $[Ir(CH_3)I_3(CO)_2]^-H^+$, $Ir(CO)_{12}$, $IrCl_3 \cdot 4H_2O$, $IrBr_3 \cdot 4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$ and hexachloroiridic acid $H_2[IrCl_3]$ preferably chloride-free complexes of iridium such as acetates, oxalates and acetoacetates.

Preferably the concentration of the catalyst in the liquid reaction composition is in the range from 50 to 5000 ppm by weight of the metal, preferably 100 to 1500 ppm by weight of the metal.

Optionally one or more promoters may be present in the liquid reaction composition. The choice of promoter will to some extent depend upon the nature of the catalytic metal employed. Using iridium as catalyst the use of metal promoters is preferred. The metal promoter may suitably be one or more of osmium, rhenium, ruthenium, cadmium, mercury, zinc, gallium, iridium and tungsten. Preferably the promoter is selected from ruthenium and osmium and more preferably is ruthenium. The promoter may comprise any promoter metal-containing compound which is soluble in the liquid reaction composition. The promoter may be added to the liquid reaction composition in any suitable form which dissolves in the liquid reaction composition or is convertible to soluble form. Examples of suitable promoter metal-containing compounds include carboxylate salts, for example acetates and carbonyl complexes. Preferably choride-free compounds are employed. Preferably the promoter metal compounds are free of impurities which provide or generate in-situ ionic iodides which may inhibit the reaction in the presence of iridium catalysts, for example alkali or alkaline earth metal or other metal salts.

Preferably the metal promoter is present in an effective amount up to the limit of its solubility in the liquid reaction composition. The promoter is suitably present in the liquid reaction composition at a molar ratio of each promoter (when present): iridium in the range [0.1 to 100:1]. Preferably [greater than 0.5]:1, more preferably [up to 15]:1 and yet more preferably [up to 10]: 1. The beneficial effect of a promoter such as ruthenium has been found to be greatest at the water concentration which gives the maximum carbonylation rate at any defined methyl acetate and methyl iodide concentration. A suitable promoter concentration is from 400 to 5000 ppm. Similar molar ratios of promoter:metal may be used in relation to Group VIII noble metals other than iridium.

Using rhodium as the carbonylation catalyst the use of iodide promoters is preferred. Both inorganic and organic iodides may be employed. Suitable inorganic iodides include alkali metal and alkaline earth metal iodides. A preferred metal iodide is lithium iodide. The iodides may be added as such or in the form of salts, for example carboxylate salts, such as acetates, which are convertible to iodides under carbonylation conditions. Alternatively organic iodides, suitably selected from quaternary ammonium, pyridinium and picolinium iodides may be employed.

The carbon monoxide feed to the carbonylation process may be essentially pure or may contain impurities such as carbon dioxide, methane, nitrogen, noble gases, water and $C_1$ to $C_4$ paraffinic hydrocarbons. The presence of hydrogen in the carbon monoxide is not generally desirable. The partial pressure of carbon monoxide in the carbonylation reaction vessel may suitably be in the range from 1 to 70 barg, preferably from 1 to 35 barg, more preferably from 1 to 15 barg.

The total pressure of the carbonylation process is suitably in the range 10 to 100 barg, preferably 10 to 50 barg. The temperature at which the carbonylation process is operated is suitably in the range from 100 to 300° C., preferably in the range form 150 to 220° C.

The method of the present invention is particularly applicable to the use of iridium carbonylation catalysts in the presence of ruthenium and/or osmium, preferably ruthenium, as catalyst promoter, because of the high carbonylation rates achievable with such catalysts.

Figure 2:
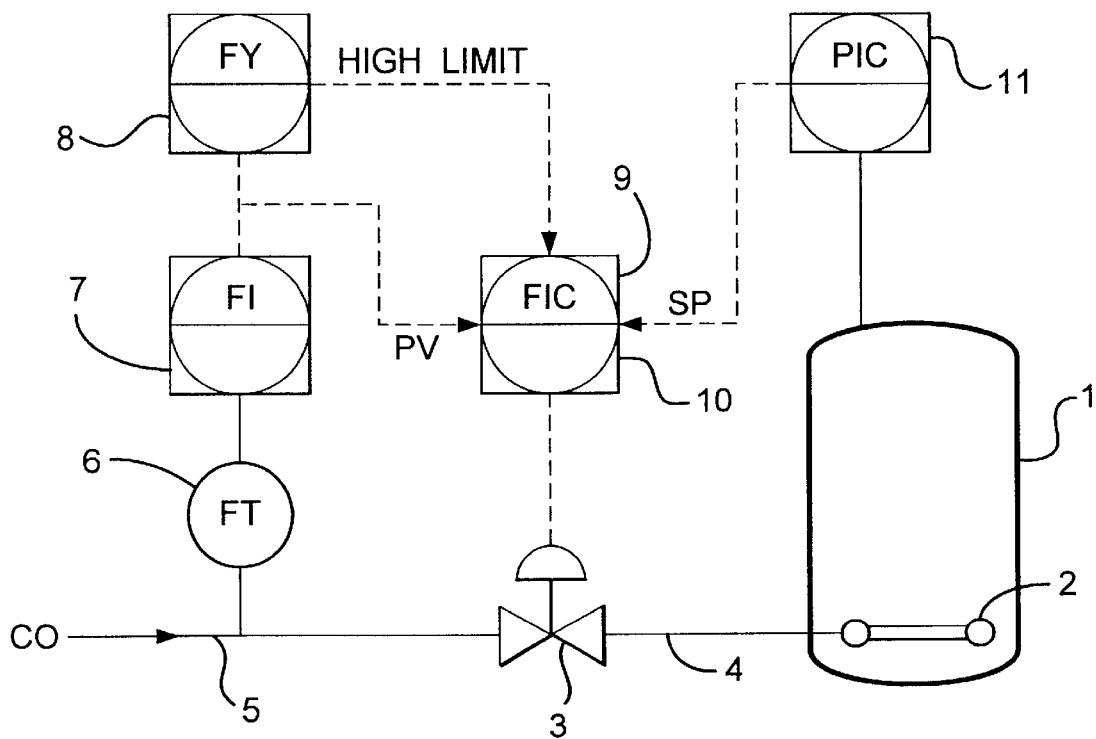
Figure 3:
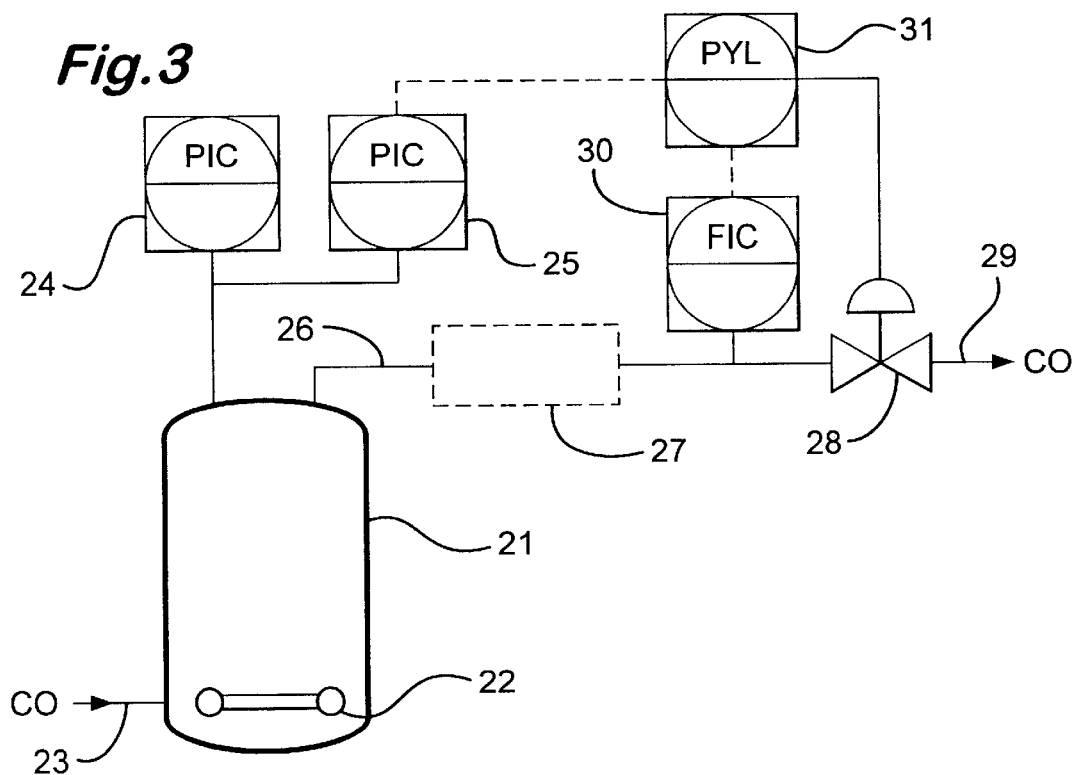
Figure 4:
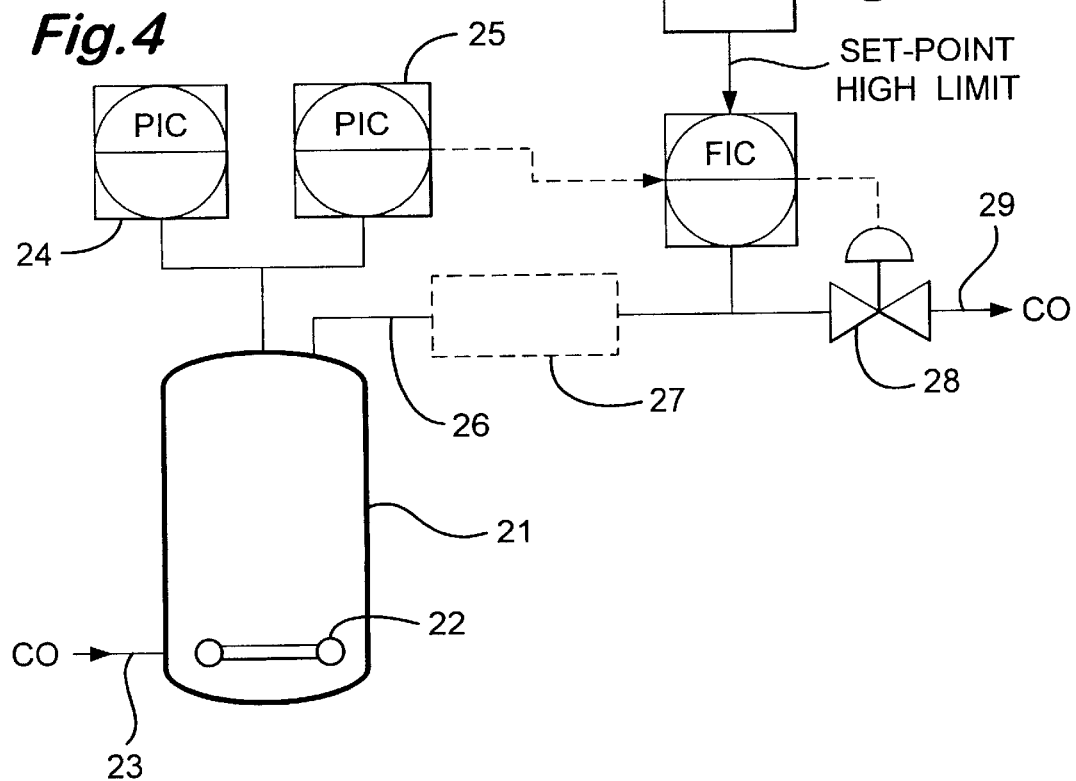

The method of the present invention will now be further described by reference to the accompanying Figures in which FIGS. 1 and 2 are schematic representations of two means for achieving controlled carbon monoxide flow to a carbonylation reactor and FIGS. 3 and 4 are schematic representations of two means for achieving reactor pressure control by controlling the flow of high pressure vent gas.

With reference to FIG. 1:

1 is a reactor wherein acetic acid is produced continuously by feeding carbon monoxide and methanol and/or a reactive derivative thereof, there being maintained in the reactor a liquid reaction composition comprising at least 5% w/w, typically at least 8% w/w, methyl acetate, a finite concentration of water, from 1 to 30% w/w methyl iodide, a Group VIII noble metal catalyst, optionally at least one promoter and acetic acid comprising the remainder of the composition, 2 is a carbon monoxide sparger within the reactor 1, 3 is a carbon monoxide flow control valve communicating through line 4 with the sparger 2, 5 is a carbon monoxide feed line communicating with a source of carbon monoxide (not shown), 6 is a flow transmitter, 7 is a flow indicator, 8 is a calculation block, 9 is flow controller, 10 is a signal selector, and 11 is a pressure controller.

In the alternative scheme illustrated in FIG. 2 the same reference numerals are employed. In this scheme, however, there is no signal selector 10.

Operation of the method of the invention will now be described with reference to FIG. 1. Under normal conditions carbon monoxide is fed through line 5, via the flow control valve 3 and the feed line 4 to the sparger 2 within the reactor 1, the flow rate through the valve 3 being controlled by the pressure controller 11.

The flow rate of carbon monoxide through the valve 3 is measured by the flow transmitter 6 and is fed to the calculation block 8 where its average value over the preceding 10 minutes is calculated and to this value is added a constant amount to give a maximum carbon monoxide flow rate which in turn is fed as a set point to the flow controller 9. Normally, the carbon monoxide flow rate to the reactor through the valve 3 is regulated by the pressure controller 11 because the rate as measured by the flow transmitter 6 is below the maximum carbon monoxide flow rate and therefore below the set point in the carbon monoxide flow controller 9. Under these conditions the flow controller 9 is inoperative.

However, in the event of a reactor disturbance involving higher carbon monoxide uptake in the reactor the flow through valve 3 would increase beyond the maximum flow rate as calculated were it not for the fact that the selector 10 switches to controlling the carbon monoxide flow rate through the valve 3 by means of the flow controller 9, the set point of which prevents the flow exceeding the maximum allowable rate. By this means the flow is regulated and eventually returns through the selector to pressure control.

In the scheme shown in FIG. 2 there is no selector 10 and the flow controller 9 is in permanent charge of operation of the valve 3. In this case the calculation block 8 sets a value for the maximum allowable carbon monoxide flow such that the flow through the valve 3 does not exceed this value.

FIGS. 3 and 4 illustrate schemes for carbon monoxide vent flow control which may be used to supplement the carbon monoxide input reactor controls as described hereinbefore.

With reference to FIG. 3, 21 is a carbonylation reactor, 22 is a carbon monoxide sparger communicating through line 23 with a supply of carbon monoxide, 24 is a first pressure controller, 25 is a second pressure controller, 26 is a carbon monoxide vent line from the reactor 21, 27 is an optional methyl iodide removal assembly, 28 is a high pressure vent gas control valve, 29 is a gas vent, 30 is a flow controller and 31 is a signal selector.

With reference to FIG. 4, the numerals 21 to 30 are identical to those in FIG. 1. However, instead of denoting a signal selector the numeral 31 denotes an input block producing a set point high limit.

With reference to FIG. 3, the high pressure vent gas control valve (28) is activated through the signal selector (31) responsive to inputs from either the flow controller (30) or the second pressure controller (25), the second pressure controller being governed by a set-point which is below the pressure of the first pressure controller (24), the output from to the signal selector (31) and hence operation of the control valve (28) is defined by the flow controller (30) when the reactor pressure is equal to or above the set-point of the second pressure controller (25).

This may also be achieved by means of a set-point high limit to the high pressure vent gas control valve (28) by the arrangement as shown in FIG. 4.

What is claimed is:

1. A method of controlling the carbon monoxide flow to a reactor wherein acetic acid is produced continuously by feeding carbon monoxide through a control valve and methanol and/or a reactive derivative thereof, there being maintained in the reactor a liquid reaction composition comprising at least 5% w/w methyl acetate, a finite concentration of water, from 1 to 30% w/w methyl iodide, a Group VIII noble metal catalyst, optionally at least one promoter and acetic acid comprising the remainder of the composition which method comprises the steps of:

(i) measuring the carbon monoxide flow through the control valve;
   (ii) performing a background calculation to arrive at a time-averaged carbon monoxide flow rate;
   (iii) adding a constant value to the time-averaged carbon monoxide flow to arrive at a maximum allowable carbon monoxide flow rate; and
   (iv) feeding information comprising the calculated maximum allowable carbon monoxide flow rate to a control system which operates in a manner such that the carbon monoxide flow rate to the reactor can not exceed the calculated maximum flow rate at any time.

2. A method as claimed in claim 1 wherein the control valve is activated through a low signal selector responsive to inputs from either a reactor pressure controller or a carbon monoxide feed flow controller.

3. A method as claimed in claim 1 wherein the maximum allowable carbon monoxide flow rate ($FC_{sp}$) is calculated according to the formula $$FC_{sp}=Fav+X$$

wherein Fav is the carbon monoxide flow (in tons/hour) over a specified immediately preceding time period; and X is a pre-determined amount in the range of from 0.1 to 1.0 tons/hour.

4. A method as claimed in claim 1 wherein the Group VIII noble metal catalyst is rhodium or iridium.

5. A method as claimed in claim 2 wherein the Group VIII noble metal catalyst is rhodium or iridium.

6. A method as claimed in claim 3 wherein the Group VIII noble metal catalyst is rhodium or iridium.

7. A method according to claim 4 wherein the catalyst in the liquid reaction composition is in the range from 50 to 5000 ppm by weight of the metal.

8. A method according to claim 6 wherein the catalyst in the liquid reaction composition is in the range from 50 to 5000 ppm by weight of the metal.

9. A method as claimed in claim 1 wherein the promoter is selected from metal promoters, inorganic iodides and organic iodides.

10. A method as claimed in claim 1 wherein water is present in a concentration of from 0.1 to 30% w/w.

11. A method as claimed in claim 1 carried out under a pressure of from 10 to 100 barg and a temperature of from 100 to 300° C.

12. A method as claimed in claim 2, wherein the maximum allowable carbon monoxide flow rate ($FC_{sp}$) is calculated according to the formula $$FC_{sp}=Fav+X$$

wherein Fav is the carbon monoxide flow (in tons per hour) over a specified immediately preceding time period; and X is a pre-determined amount in the range of from 0.1 to 1.0 tons/hour.

* * * * *